(12) United States Patent
Walborn (10) Patent No.: US 7,201,739 B2
(45) Date of Patent: Apr. 10, 2007

(54) CATHETER SUPPORT APPARATUS AND METHOD

(76) Inventor: Carol Margaret Walborn, 107 Saratoga Trail, Chapel Hill, NC (US) 27516

( * ) Notice: Subject to any disclaimer, the term of this patent is extended or adjusted under 35 U.S.C. 154(b) by 0 days.

(21) Appl. No.: 10/975,651

(22) Filed: Oct. 28, 2004

(65) Prior Publication Data
US 2005/0182367 A1 Aug. 18, 2005

Related U.S. Application Data

(60) Provisional application No. 60/545,152, filed on Feb. 17, 2004.

(51) Int. Cl.
*A61M 5/00* (2006.01)
(52) U.S. Cl. .................................... 604/178
(58) Field of Classification Search ............... 604/174, 604/178, 180, 179, 333, 523, 905; 606/194, 606/41; 128/DIG. 26, 207.14; 600/18
See application file for complete search history.

(56) References Cited

U.S. PATENT DOCUMENTS

| | | | |
|---|---|---|---|
| 4,578,062 A | | 3/1986 | Schneider |
| 4,582,508 A | * | 4/1986 | Pavelka ...................... 604/179 |
| 4,666,432 A | | 5/1987 | McNeish et al. |
| 4,726,716 A | * | 2/1988 | McGuire ..................... 604/180 |
| 5,048,122 A | | 9/1991 | Prieur |
| 5,271,745 A | * | 12/1993 | Fentress et al. ............. 604/179 |
| 5,664,581 A | * | 9/1997 | Ashley ....................... 128/876 |
| 5,709,665 A | | 1/1998 | Vergano et al. |
| 5,755,698 A | | 5/1998 | Kagan et al. |
| 6,224,571 B1 | * | 5/2001 | Bierman ..................... 604/174 |
| 6,247,211 B1 | | 6/2001 | Bell |
| 6,477,710 B1 | | 11/2002 | Ojoyeyi |
| 6,579,268 B1 | | 6/2003 | Loining |

OTHER PUBLICATIONS

International Search Report with Written Opinion dated Jun. 27, 2006.
International Preliminary Report on Patentability dated Aug. 31, 2006.

* cited by examiner

*Primary Examiner*—Nickolas D. Lucchesi
*Assistant Examiner*—Christopher D Koharski
(74) *Attorney, Agent, or Firm*—Jenkins, Wilson, Taylor & Hunt, P.A.

(57) ABSTRACT

Apparatuses and methods for holding and supporting an intravenous catheter are disclosed, wherein the catheter support apparatus is adjustable and can be removed easily and rapidly. The catheter support apparatus includes an elongate member comprising a first end, an opposed second end, and a central portion located between the first end and the second end; a foldable strip member attached to the first end of the elongate member and adapted for movement between an open and a closed position; an attachment element adapted for removeably securing the second end on the elongate member to the inside surface of the strip member; and a closure element adapted for removeably securing the strip member in a closed position wherein the inside surface of the strip member is adapted for slidably engaging and supporting a portion of the exposed segment of the catheter.

36 Claims, 5 Drawing Sheets

CATHETER SUPPORT APPARATUS AND METHOD

RELATED APPLICATIONS

This application claims the benefit of U.S. Provisional Patent Application Ser. No. 60/545,152, filed Feb. 17, 2004; the disclosure of which is incorporated herein by reference in its entirety.

TECHNICAL FIELD

The subject matter disclosed herein relates generally to medical devices. More particularly, the present subject matter relates to apparatuses and methods for holding and supporting an intravenous catheter wherein the catheter support apparatus is adjustable and can be removed easily and rapidly.

BACKGROUND ART

As a result of various medical procedures, it is often necessary and desired to have repeated and frequent access to a patient's circulation system for the delivery of blood and intravenous solutions. Apparatuses and procedures have been developed to allow such access while avoiding repeated venipuncture by using various types of catheters.

One type catheter is the tunneled central venous catheter, such as the Hickman indwelling atrial catheter designed many years ago by Robert O. Hickman. The Hickman catheter provides ready access to the patient's circulation both for drawing blood and for administering drugs, blood products and total paranterol nutrition. The use of the catheter can also provide added comfort to patients wherein outpatients can be sent home with the catheter in place for later follow-up use.

The catheter is basically comprised of a long tube which is inserted into a central vein inside the patient's chest. The tube then extends from the vein to outside of the patient's chest where a coupling is attached to the outside end of the tube. The external end of the coupling is threaded and has a port through which injections or transfusions can be administered directly, allowing less chance of contamination and air embolism.

The Hickman catheter is available in single and multiple lumen catheter configurations wherein the multiple lumen models are comprised of two or more couplings that are attached to the insertion tube. Since the multiple lumen models have two or more couplings attached to the end of the tube, they are somewhat heavier than the single lumen Hickman catheter, however these multiple lumen catheters are extremely popular with physicians since drugs, such as those used in chemotherapy, can be administered through one coupling while blood or paranterol nutrition can be administered through the other coupling at the same time.

When using either the single or multiple lumen catheter, the catheter is implanted inside the patient and as such may remain implanted for months at a time. The free end of the catheter extending outwardly from the patient's body often causes problems for the patient when attempting to carry out normal daily activities. For example, the free end of the catheter, while attached to IV lines, can catch or snag on objects when a patient walks by or on articles of clothing the patient is wearing. It is imperative that the catheter be prevented from catching on any objects or articles of clothing the patient may wear to ensure that the incision through which the catheter extends into the body is not ruptured or the catheter dislodged from the incision. Furthermore, constant rubbing or movement of the catheter within the incision may lead to serious complications from resulting infection.

The most common method used to support the catheter and prevent movement is to tape the assembly directly onto the patient's skin. However, after repeatedly removing the tape to clean the sterile site and to use the catheter, the patient's skin becomes sensitive to the point that it can bleed and it may also be extremely painful to remove or apply the support tape.

Efforts have been made in the past to eliminate the need to employ medical tape to secure the external portion of the implanted catheter to the skin of a patient. U.S. Pat. No. 5,048,122 to Prieur and U.S. Pat. No. 6,477,710 to Ojoveyi are each directed to a garment to be worn by a person with an implanted catheter line for concealing and storing of the catheter line on the inside of the garment. U.S. Pat. No. 4,578,062 to Schneider, U.S. Pat. No. 4,666,432 to McNeish et al., and U.S. Pat. No. 5,755,698 to Kagan et al. are each directed to catheter protector harnesses that comprise a belt encircling the body from the chest to the back by passing under the arms and which have at least one strip passing over the shoulder wherein the catheter is enclosed within the harness device. U.S. Pat. No. 4,582,508 to Pavelka is directed to a garment for holding, storing, supporting and receiving indwelling catheters wherein the garment comprises straps to hold the garments securely to a patient's body, a pocket element within which to store the catheter, and fastening means to connect the straps and the pocket elements. Finally, U.S. Pat. No. 6,579,268 to Loining discloses a pouch for releasably securing a free end of a catheter extending outwardly from the body of an individual wherein at one end the pouch includes a releasable clip adapted to secure the pouch to an article of clothing worn by the individual and further wherein the pouch also includes at least one releasable closure and enables the patient to selectively open and close the pouch in order to insert and remove the free end of the catheter from the pouch. While these prior art catheter supports have had limited success in different environments, there remains a need for a catheter support apparatus which can comfortably hold the catheter in a stationary position on a patient in order to avoid irritation of or damage to the incision, avoid dislodging of the catheter, that may be used at all times by the patient (i.e., whether they are wearing clothing articles or not), and that also is able to be rapidly released in the case of an emergency.

SUMMARY

According to one embodiment, a catheter support apparatus for supporting an exposed segment of a catheter is provided comprising an elongate member comprising a first end, an opposed second end, and a central portion located between the first end and the second end. The catheter support apparatus further comprises a foldable strip member attached to the first end of the elongate member and adapted for movement between an open and a closed position wherein the foldable strip member comprises an inside surface, an outside surface, top, bottom, left and right side edges, and a longitudinal fold located between the left side edge and the right side edge for separating the strip member into left and right portions wherein the right portion is folded onto the left portion when the strip member is in the closed position. The catheter support apparatus further comprises an attachment element adapted for removably securing the second end of the elongate member to the inside surface of the strip member and a closure element adapted for removably securing the strip member in a closed position wherein the inside surface of the strip member is adapted for slideably engaging and supporting a portion of the exposed segment of the catheter.

According to another embodiment, a method for supporting an exposed segment of a catheter implanted in the body of a patient is provided comprising providing a catheter support apparatus as described above, positioning the central portion of the elongate member around the patient's neck area, removably securing the second end of the elongate member to the inside surface of the left portion of the strip member, positioning a portion of the exposed segment of the catheter along the longitudinal fold on the inside surface of the strip member, and folding the right portion of the strip member onto the left portion wherein the strip member is removably secured in the closed position and the catheter is supported.

It is therefore an object to provide catheter support apparatuses and methods for supporting an exposed segment of a catheter wherein the catheter support apparatus can be worn at all times by the patient, yet is able to be immediately released in emergency situations.

An object having been stated hereinabove, and which is achieved in whole or in part by the subject matter disclosed herein, other objects will become evident as the description proceeds when taken in connection with the accompanying drawings as best described hereinbelow.

DETAILED DESCRIPTION

Figure 1A:
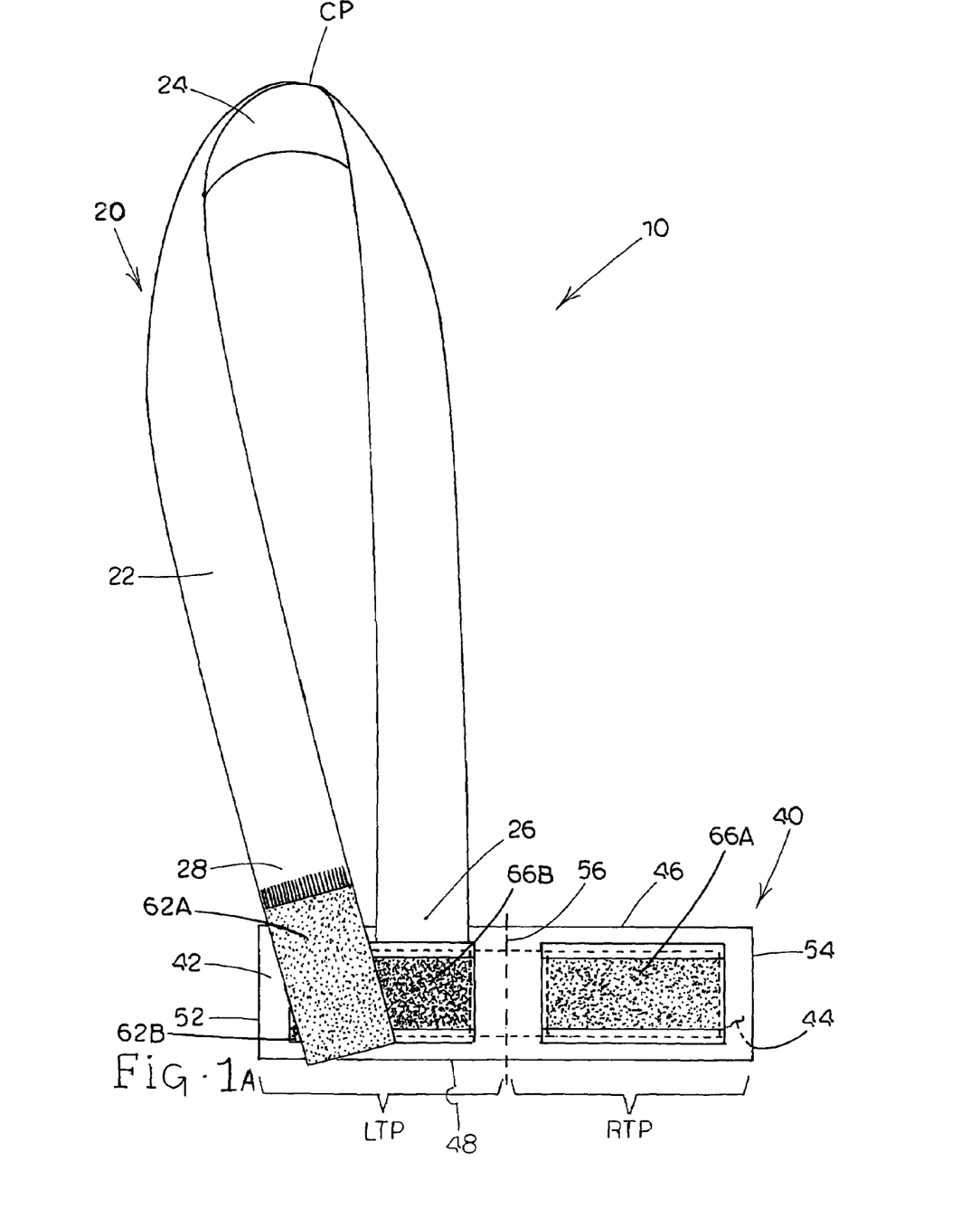
FIGS. 1A and 1B are front plan views of a catheter support apparatus in accordance with two embodiments of the present subject matter.
Figure 1B:
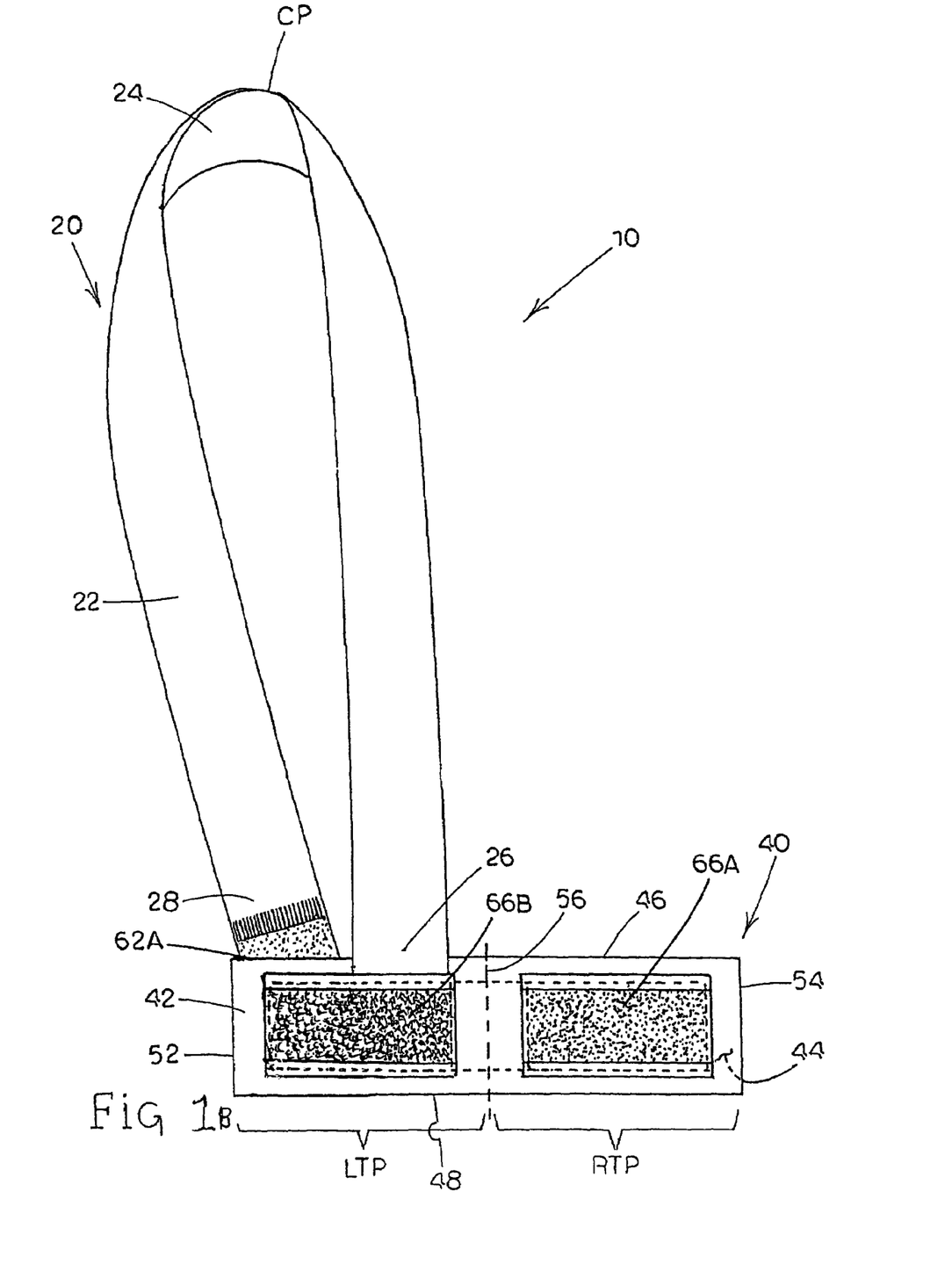

Referring now to FIG. 1A, an exemplary embodiment of the catheter support apparatus of the present subject matter is shown generally as 10. Catheter support apparatus 10 is designed for supporting the catheter lumen CL of a catheter C that is implanted in the body of a patient P. Catheter support apparatus 10 comprises an elongate member 20 designed to encircle the neck area N of a patient P. The elongate member comprises a first end 26, an opposed second end 28, and a central portion CP that is located between first end 26 and second end 28. In the exemplary embodiment, elongate member 20 comprises a strip of material having a first side surface 22 and second side surface 24 as shown in FIG. 1 wherein the width dimension of the strip is approximately 1 inch and the length dimension is in the range of 12 inches to 28 inches. However, it is also envisioned that elongate member 20 may comprise a cord (see FIG. 2) of any cross-sectional shape or any other hanging-type member. Elongate member 20 may be constructed of cloth-like material, including cotton, polycotton blends, and elastic and non-elastic fabrics, rubber-like material, and paper-like material. A disposable version of catheter support apparatus 10 may also include an elongate member 20 constructed of natural or synthetic nonwovens wherein the natural nonwovens may include cotton, hemp, flax, jute, and wood pulp and the synthetic nonwovens may include polypropylene, polystyrene, polyethylene, nylon, and polyester. Other materials known to those of skill in the art may also be used to construct elongate member 20. Finally, it is envisioned that elongate member 20 may be tied or cut to adjust for length when used according to the method discussed hereinbelow.

Catheter support apparatus 10 further comprises a foldable strip member generally shown as 40 that is attached to first end 26 of elongate member 20 and that is adapted for movement between an open position and a closed position. Foldable strip member 40 comprises an inside surface 42, outside surface 44, top side edge 46, bottom side edge 48, left side edge 52, and right side edge 54. Foldable strip member 40 further comprises a longitudinal fold 56 located between left side edge 52 and right side edge 54, preferably equidistant between left side edge 52 and right side edge 54. Longitudinal fold 56 separates foldable strip member 40 into left portion LTP and right portion RTP. The preferable equidistant positioning of longitudinal fold 56 allows for right portion RTP to be folded onto left portion LTP when foldable strip member 40 is in the closed position. Similar to the construction of elongate member 20 discussed hereinabove, foldable strip member 40 may be constructed of cloth-like material, rubber-like material, paper-like material, and disposable material such as natural or synthetic nonwovens. Additionally, foldable strip member 40 may be constructed in the shape of a rectangle (FIG. 1), a circle (FIG. 2), or any other shape compatible with the use of the present subject matter and may be tapered at one or more ends. In the exemplary embodiment, the dimensions of foldable strip member 40 are approximately 4 inches wide by approximately 1 inches high in the open position and approximately 2 inches wide by approximately 1 inches high in the closed position.

It is envisioned that foldable strip member 40 and elongate member 20 may be one unbroken piece, such as in a disposable version. Additionally, foldable strip member 40 and elongate member 20 may be two separate pieces wherein foldable strip member 40 is attached to first end 26 of elongate member 20 by sewing, stapling, gluing, heat fusing, or any other method known to those of skill in the art.

Catheter support apparatus 10 also comprises an attachment element 62 adapted for removeably securing second end 28 of elongate member 20 to foldable strip member 40. In the exemplary embodiment, attachment element 62 may comprise a first attachment portion 62A that is attached to second end 28 of elongate member 20 and a second attachment portion 62B that is attached to inside surface 42 of left portion LTP of foldable strip member 40 and that is interlockable with first attachment portion 62A. As an example, attachment element 62 may comprise hook and loop material wherein the hook material may be first attachment portion 62A attached to second end 28 of elongate member 20 and the loop material may be second attachment portion 62B attached to inside surface 42 of left portion LTP of strip member 40. In use, second attachment portion 62A allows elongate member 20 to be adjusted by the patient to a desired length and also creates a breakaway feature that allows rapid release of the device. It is also envisioned that second end 28 of elongate member 20 may be removeably secured to outside surface 44 of foldable strip member 40 by attachment element 62 wherein a second attachment portion 62B is attached to outside surface 44 of left portion LTP of foldable strip member 40 and is interlockable with first attachment portion 62A that is attached to elongate member second end 28.

Catheter support apparatus 10 further comprises a closure element 66 that is adapted for removeably securing foldable strip member 40 in a closed position wherein inside surface 42 of strip member 40 is adapted for slidingly engaging and supporting a portion of the exposed segment of catheter C. Closure element 66 may comprise a first closure portion 66A that is attached to inside surface 42 of right portion RTP of strip member 40 and a second closure portion 66B that is attached to inside surface 42 of left portion LTP of strip member 40 and that is interlockable with first closure portion 66A.

Figure 2:
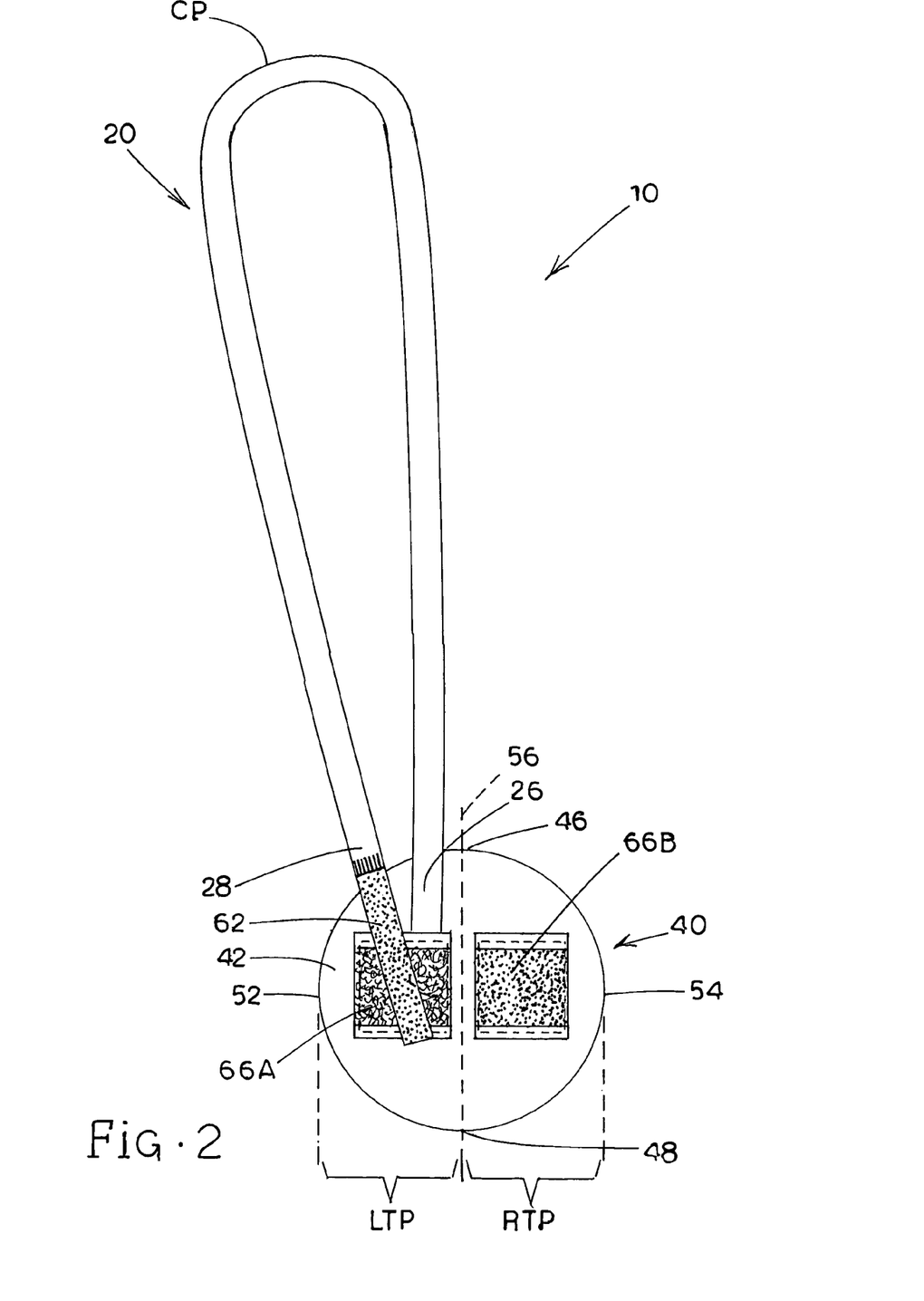
FIG. 2 is a front plan view of a catheter support apparatus provided in accordance with another embodiment of the present subject matter.

For example, as shown in FIGS. 1 and 2, closure element 66 may be constructed of hook and loop material wherein the hook material is first closure portion 66A attached to inside surface 42 of strip member right portion RTP and the loop material is second closure portion 66B attached to inside surface 42 of strip member left portion LTP and that is interlockable with first closure portion 66A.

Figure 3A:
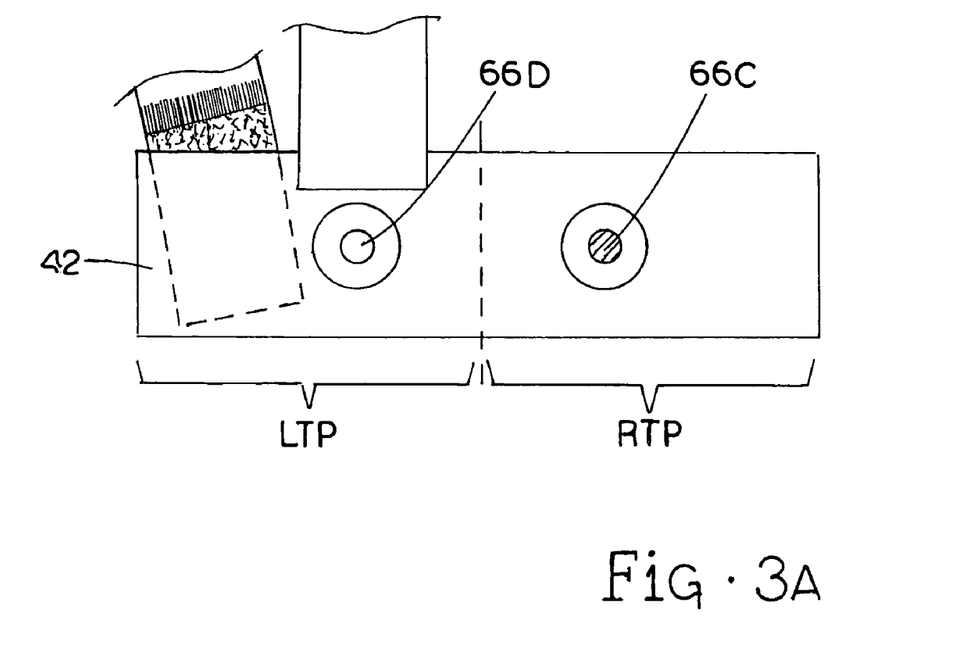
FIGS. 3A and 3B are plan views detailing various closure elements of a catheter support apparatus of the present subject matter.

It is envisioned that closure element 66 may also consist of snap fasteners, magnets, buttons, clasps, or other similar materials. For example, as shown in FIG. 3A, closure element 66 may be constructed of a snap fastener stud and socket system comprising a first closure stud portion 66C attached to inside surface 42 of strip member right portion RTP and a second closure socket portion 66D attached to inside surface 42 of strip member left portion LTP and that is interlockable with first closure portion 66C.

Figure 3B:
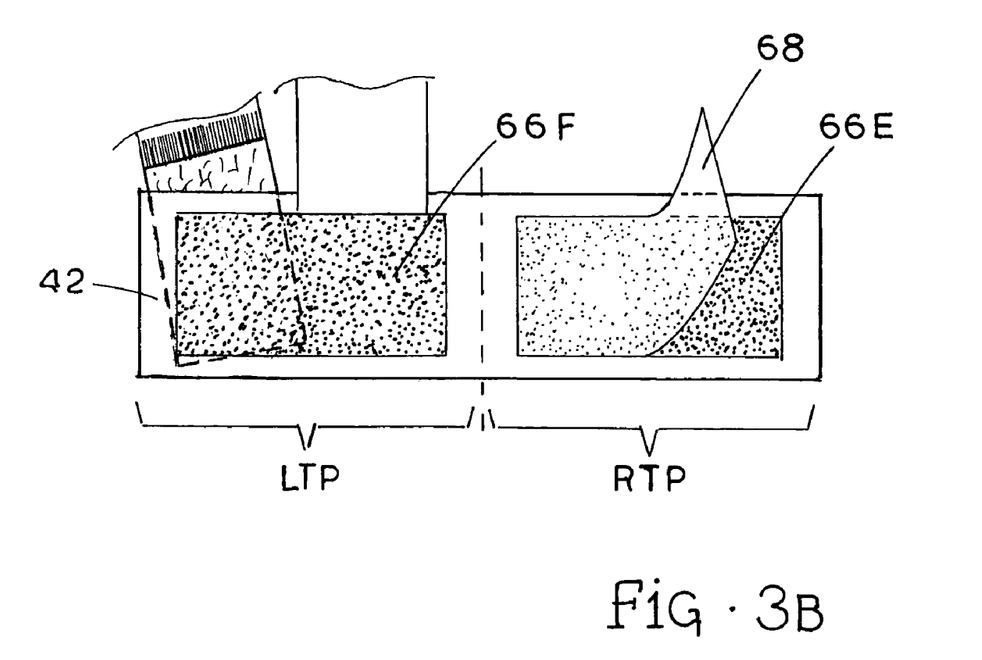

Additionally, as in a disposable version of catheter support apparatus 10 and as shown in FIG. 3B, closure element 66 may comprise a first adhesive portion 66E that is attached to inside surface 42 of strip member right portion RTP and a second adhesive portion 66F that is attached to inside surface 42 of strip member left portion LTP and that is interlockable with first adhesive portion 66E. First and second adhesive portions 66E, 66F may consist of a medical-grade adhesive adapted for repeated cleaning without degradation or any other adhesive known to those of skill in the art for such purposes. Additionally, a releasable liner 68 may be provided over first and second adhesive portions 66E, 66F for protection of the adhesive when not in use and that is adapted to be removed prior to interlocking of first adhesive portion 66E with second adhesive portion 66F.

A final method of removeably securing foldable strip member 40 in a closed position may include a tapered right edge 54 that is threaded through slits (not shown) located on strip member left portion LTP, wherein tapered right edge 54 is secured by a slipknot, loop, or similar holding arrangement.

Figure 4A:
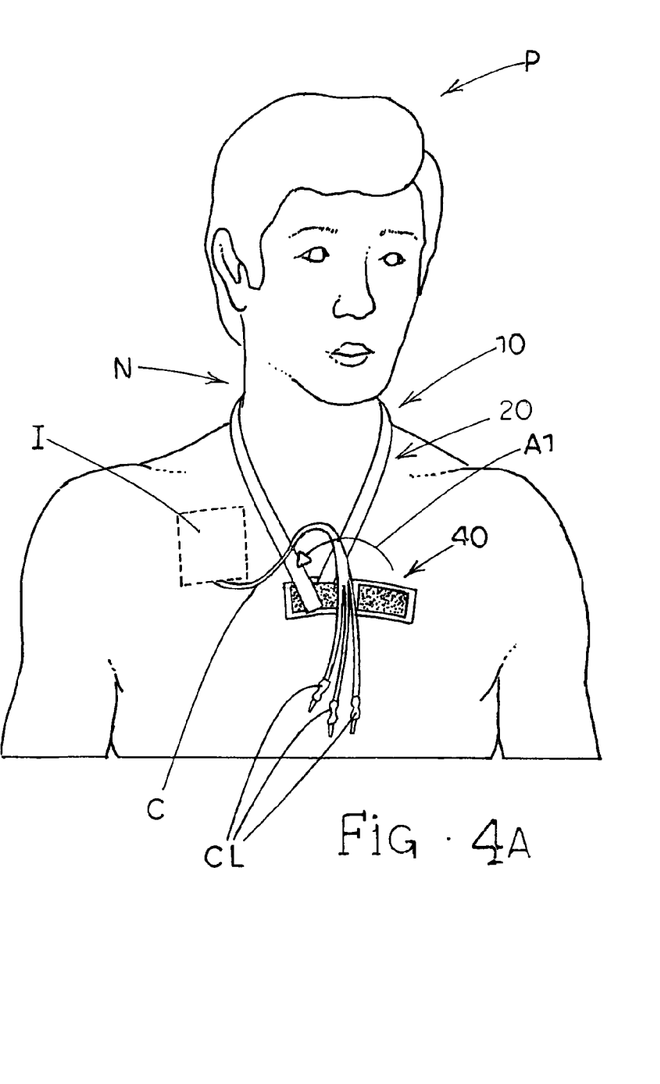
FIGS. 4A and 4B are perspective views of a patient using a catheter support apparatus providing in accordance with one embodiment of the present subject matter.
Figure 4B:
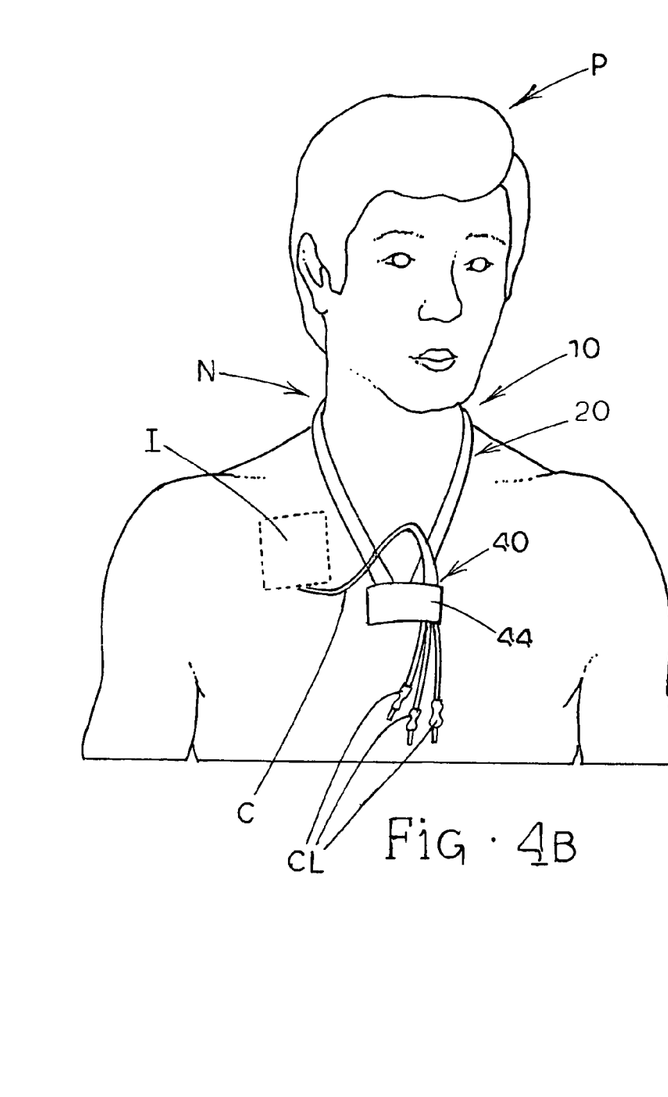

With reference to FIGS. 1, 4A and 4B, a method for supporting an exposed segment of a catheter implanted in the body of a patient utilizing the catheter support apparatus of the present subject matter will now be described. First, catheter C is implanted in the body of a patient P at implant site I by methods known to those of skill in the art. The exposed segment of catheter C, including catheter lumens CL when attached to an IV line, is subject to catching on objects or otherwise capable of pulling away from implant site I if not restrained in some manner.

The method includes providing a catheter support apparatus as described above wherein patient P will position central portion CP of elongate member 20 around neck area N such that elongate member 20 encircles neck area N with elongate member second end 28 and foldable strip member 40 (attached to elongate member first end 26) being positioned around the front chest area of patient P. Second end 28 of elongate member 20 is then removeably secured to inside surface 42 of left portion LTP of foldable strip member 40 wherein catheter support apparatus 10 is secured to patient P. Next, patient P will position a portion of the exposed segment of catheter C, including catheter lumens CL, along longitudinal fold 56 on inside surface 42 of foldable strip member 40. Right portion RTP of foldable strip member 40 is then folded onto left portion LTP in the direction of arrow A1 wherein first closure portion 66A is removeably interlocked with second closure portion 66B so that foldable strip member 40 is in the closed position. At this point, catheter C and catheter lumens CL are supported and secured from catching on objects (when attached to an IV line) or otherwise being pulled away from the patient's body. In the event that catheter C must be accessed expediently and/or catheter support apparatus 10 must be removed rapidly, the construction of attachment element 62 and closure element 66 allow foldable strip member 40 to be opened rapidly and also allow catheter support apparatus 10 to be removed from patient P rapidly.

It will be understood that various details of the invention may be changed without departing from the scope of the invention. Furthermore, the foregoing description is for the purpose of illustration only, and not for the purpose of limitation, as the invention is defined by the claims as set forth hereinafter.

What is claimed is:

1. A catheter support apparatus for supporting an exposed segment of a catheter, the catheter support apparatus comprising:
  (a) an elongate member comprising a first portion terminating at a first terminal end, an opposed second portion terminating at a second terminal end, and a central portion located between the first portion and the second portion;
  (b) a foldable strip member attached to the first terminal end of the first portion of the elongate member and adapted for movement between an open and a closed position, the foldable strip member comprising:
    (i) an inside surface and an outside surface;
    (ii) top, bottom, left and right side edges; and
    (iii) a longitudinal fold located between the left side edge and the right side edge for separating the strip member into left and right portions wherein the right portion is folded onto the left portion when the strip member is in the closed position;
  (c) an attachment element attached to the second terminal end of the second portion of the elongate member and adapted for removeably securing the second portion of the elongate member to the strip member, such that the elongate member is capable of encircling a neck of a patient; and
  (d) a closure element adapted for removeably securing the strip member in a closed position wherein the inside surface of the strip member is adapted for slidably engaging and supporting a portion of the exposed segment of the catheter.

2. The catheter support apparatus according to claim 1 wherein the elongate member comprises a cord.

3. The catheter support apparatus according to claim 1 wherein the elongate member comprises a strip having a first side surface and a second side surface.

4. The catheter support apparatus according to claim 3 wherein the width dimension is approximately 1 inch and the length dimension is in the range of 12 inches to 28 inches.

5. The catheter support apparatus according to claim 1 wherein the dimensions of the foldable strip member in the open position are approximately 4 inches wide by approximately 1 inches high.

6. The catheter support apparatus according to claim 5 wherein the dimensions of the foldable strip member in the closed position are approximately 2 inches wide by approximately 1 inches high.

7. The catheter support apparatus according to claim 1 wherein the elongate member is constructed of a material selected from the group consisting of cloth material, rubber material, paper material, and disposable material.

8. The catheter support apparatus according to claim 1 wherein the foldable strip member is constructed of a material selected from the group consisting of cloth material, rubber material, paper material, and disposable material.

9. The catheter support apparatus according to claim 7 or 8 further wherein the elongate member and the foldable strip are constructed of natural or synthetic nonwovens.

10. The catheter support apparatus according to claim 9 wherein the natural nonwovens are selected from the group consisting of cotton, hemp, flax, jute and wood pulp.

11. The catheter support apparatus according to claim 9 wherein the synthetic nonwovens are selected from the group consisting of polypropylene, polystyrene, polyethylene, nylon, and polyester.

12. The catheter support apparatus according to claim 1 wherein the longitudinal fold of the foldable strip member is located approximately equidistant between the left side edge and the right side edge.

13. The catheter support apparatus according to claim 1 wherein the foldable strip member is in the shape of a rectangle.

14. The catheter support apparatus according to claim 1 wherein the foldable strip member is in the shape of a circle.

15. The catheter support apparatus according to claim 1 wherein the attachment element comprises hook and loop material wherein a first attachment portion is attached to the second end of the elongate member and a second attachment portion is attached to the inside surface of the left portion of the strip member and is interlockable with the first attachment portion.

16. The catheter support apparatus according to claim 1 wherein the closure element is selected from the group consisting of hook and loop material, snap fasteners, magnets, buttons, and clasps.

17. The catheter support apparatus according to claim 16 wherein the hook and loop material comprises a first closure portion attached to the inside surface of the right portion of the strip member and a second closure portion attached to the inside surface of the left portion of the strip member and interlockable with the first closure portion.

18. The catheter support apparatus according to claim 16 wherein the snap fastener comprises a snap fastener stud and socket system comprising a first closure portion attached to the inside surface of the right portion of the strip member and a second closure portion attached to the inside surface of the left portion of the strip member and interlockable with the first closure portion.

19. The catheter support apparatus according to claim 1 wherein the closure element comprises a first adhesive portion attached to the inside surface of the right portion of the strip member and a second adhesive portion attached to the inside surface of the left portion of the strip member and interlockable with the first adhesive portion.

20. The catheter support apparatus according to claim 19 wherein the adhesive comprises a medical grade adhesive adapted for repeated cleaning without degradation.

21. The catheter support apparatus according to claim 19 wherein a releasable liner is provided over the first and second adhesive portions and is adapted to be removed prior to interlocking the first adhesive portion with the second adhesive portion.

22. The catheter support apparatus according to claim 1 wherein the elongate member and the foldable strip member are one unbroken piece.

23. The catheter support apparatus according to claim 1 wherein the foldable strip member is attached to the first end of the elongate member by sewing.

24. The catheter support apparatus according to claim 1 wherein the foldable strip member is attached to the first end of the elongate member by stapling.

25. The catheter support apparatus according to claim 1 wherein the foldable strip member is attached to the first end of the elongate member by gluing.

26. The catheter support apparatus according to claim 1 wherein the foldable strip member is attached to the first end of the elongate member by heat fusing.

27. The catheter support apparatus according to claim 1 wherein the second end of the elongate member is removeably secured to the inside surface of the strip member by the attachment element.

28. The catheter support apparatus according to claim 1 wherein the second end of the elongate member is removeably secured to the outside surface of the strip member by the attachment element.

29. A catheter support apparatus for supporting an exposed segment of a catheter, the catheter support apparatus comprising:
 (a) an elongate member comprising:
  (i) a first side surface and a second side surface;
  (ii) a first portion terminating at a first terminal end and an opposed second portion terminating at a second terminal end; and
  (iii) a central portion located between the first portion and the second portion;
 (b) a rectangular, foldable strip member attached by sewing to the first terminal end of the first portion of the elongate member and adapted for movement between an open and a closed position, the foldable strip member comprising:
  (i) an inside surface and an outside surface;
  (ii) top, bottom, left and right side edges; and
  (iii) a longitudinal fold located approximately equidistant between the left side edge and the right side edge for separating the strip member into left and right portions wherein the right portion is folded onto the left portion when the strip member is in the closed position;
 (c) an attachment element attached to the second terminal end of the second portion of the elongate member and adapted for removeably securing the second portion of the elongate member to the strip member, such that the elongate member is capable of encircling a neck of a patient; and
 (d) a closure element for removeably securing the strip member in a closed position wherein the inside surface of the strip member is adapted for slidably engaging and supporting a portion of the exposed segment of the catheter.

30. The catheter support apparatus according to claim 29 wherein the elongate member and the foldable strip member are constructed of a material selected from the group consisting of cloth-like material, rubber-like material, paper-like material, and disposable material.

31. The catheter support apparatus according to claim 30 further wherein the elongate member and the foldable strip member are constructed of natural or synthetic nonwovens.

32. The catheter support apparatus according to claim 31 wherein the natural nonwovens are selected from the group consisting of cotton, hemp, flax, jute and wood pulp.

33. The catheter support apparatus according to claim 31 wherein the synthetic nonwovens are selected from the group consisting of polypropylene, polystyrene, polyethylene, nylon, and polyester.

34. The catheter support apparatus according to claim 29 wherein the attachment element comprises hook and loop material wherein a first attachment portion is attached to the second end of the elongate member and a second attachment portion is attached to the inside surface of the left portion of the strip member and is interlockable with the first attachment portion.

35. The catheter support apparatus according to claim 29 wherein the closure element comprises hook and loop material wherein a first closure portion is attached to the inside surface of the right portion of the strip member and a second closure portion is attached to the inside surface of the left portion of the strip member and interlockable with the first closure portion.

36. A method for supporting an exposed segment of a catheter implanted in the body of a patient comprising:
 (a) providing a catheter support apparatus comprising:
  (i) an elongate member comprising a first portion terminating at a first terminal end, an opposed second portion terminating at a second terminal end, and a central portion located between the first portion and the second portion;
  (ii) a foldable strip member attached to the first terminal end of the first portion of the elongate member and adapted for movement between an open and a closed position, the foldable strip member comprising an inside surface, an outside surface, and top, bottom, left and right side edges and further comprising a longitudinal fold located between the left side edge and the right side edge for separating the strip member into left and right portions wherein the right portion is folded onto the left portion when the strip member is in the closed position;
  (iii) an attachment element attached to the second terminal end of the second portion of the elongate member and adapted for removeably securing the second portion of the elongate member to the strip member; and
  (iv) a closure element adapted for removeably securing the strip member in a closed position wherein the inside surface of the strip member is adapted for slidably engaging and supporting a portion of the exposed segment of the catheter;
 (b) positioning the central portion of the elongate member around a patient's neck area;
 (c) removeably securing the second portion of the elongate member to the left portion of the strip member;
 (d) positioning a portion of the exposed segment of the catheter along the longitudinal fold on the inside surface of the strip member; and
 (e) folding the right portion of the strip member onto the left portion wherein the strip member is removeably secured in the closed position and the catheter is supported.

* * * * *